United States Patent [19]

Iijima et al.

[11] Patent Number: 5,656,498
[45] Date of Patent: Aug. 12, 1997

[54] FREEZE-DRIED BLOOD CELLS, STEM CELLS AND PLATELETS, AND MANUFACTURING METHOD FOR THE SAME

[75] Inventors: Tetsuo Iijima, Tokyo; Yoshikazu Ishii, Hoya; Nobuhiro Funakoshi, Naka-gun; Keiji Okada, Tokyo, all of Japan

[73] Assignee: Nippon Telegraph and Telephone Corporation, Japan

[21] Appl. No.: 390,957

[22] Filed: Feb. 21, 1995

[30] Foreign Application Priority Data

Feb. 22, 1994 [JP] Japan .................................. 6-046531
Feb. 22, 1994 [JP] Japan .................................. 6-046551
Aug. 19, 1994 [JP] Japan .................................. 6-216683

[51] Int. Cl.$^6$ .......................... G01N 31/00; A01N 1/02
[52] U.S. Cl. ................... 436/10; 436/8; 435/2; 435/260; 34/304
[58] Field of Search ..................... 436/8, 10; 435/2, 435/260; 34/304

[56] References Cited

U.S. PATENT DOCUMENTS

| | | | |
|---|---|---|---|
| 3,228,838 | 1/1966 | Rinfret et al. | 34/284 |
| 3,928,566 | 12/1975 | Briggs et al. | 424/94.3 |
| 4,329,787 | 5/1982 | Newton | 34/254 |
| 4,874,690 | 10/1989 | Goodrich, Jr. et al. | 435/2 |
| 5,171,661 | 12/1992 | Goodrich, Jr. et al. | 435/2 |
| 5,364,756 | 11/1994 | Livesey et al. | 435/2 |

FOREIGN PATENT DOCUMENTS

| | | |
|---|---|---|
| 59-139959 | 8/1984 | Japan . |
| 60-251948 | 12/1985 | Japan . |
| 62-45365 | 2/1987 | Japan . |
| 62-201665 | 9/1987 | Japan . |

OTHER PUBLICATIONS

"Cryogenec Preservation of Erythrocytes by a Droplet Freezing Technique", Journal of Hokkaido University School of Medicine, T. Sato, vol. 58, No. 2, pp. 144–153 (1983).

Japanese Patent Application, Second Publication Hei 3-57831.

*Primary Examiner*—Arlen Soderquist
*Attorney, Agent, or Firm*—Finnegan, Henderson, Farabow, Garrett & Dunner, L.L.P.

[57] ABSTRACT

The present invention provides a method for manufacturing freeze-dried blood cells, stem cells and platelets comprising the steps of: pre-treating a liquid selected from the group consisting of blood including blood cells, bone marrow fluid (hemopoietic stem cells), and platelets in blood plasma, with a solution containing at least one substance selected from the group consisting of saccharide, biopolymer, acid and acid salt; conducting granulation of the aforementioned pre-treated liquid into a granules of a predetermined size; performing rapid cooling of the granules; and drying the resultant frozen material by sublimation of the water content contained therein.

16 Claims, 4 Drawing Sheets

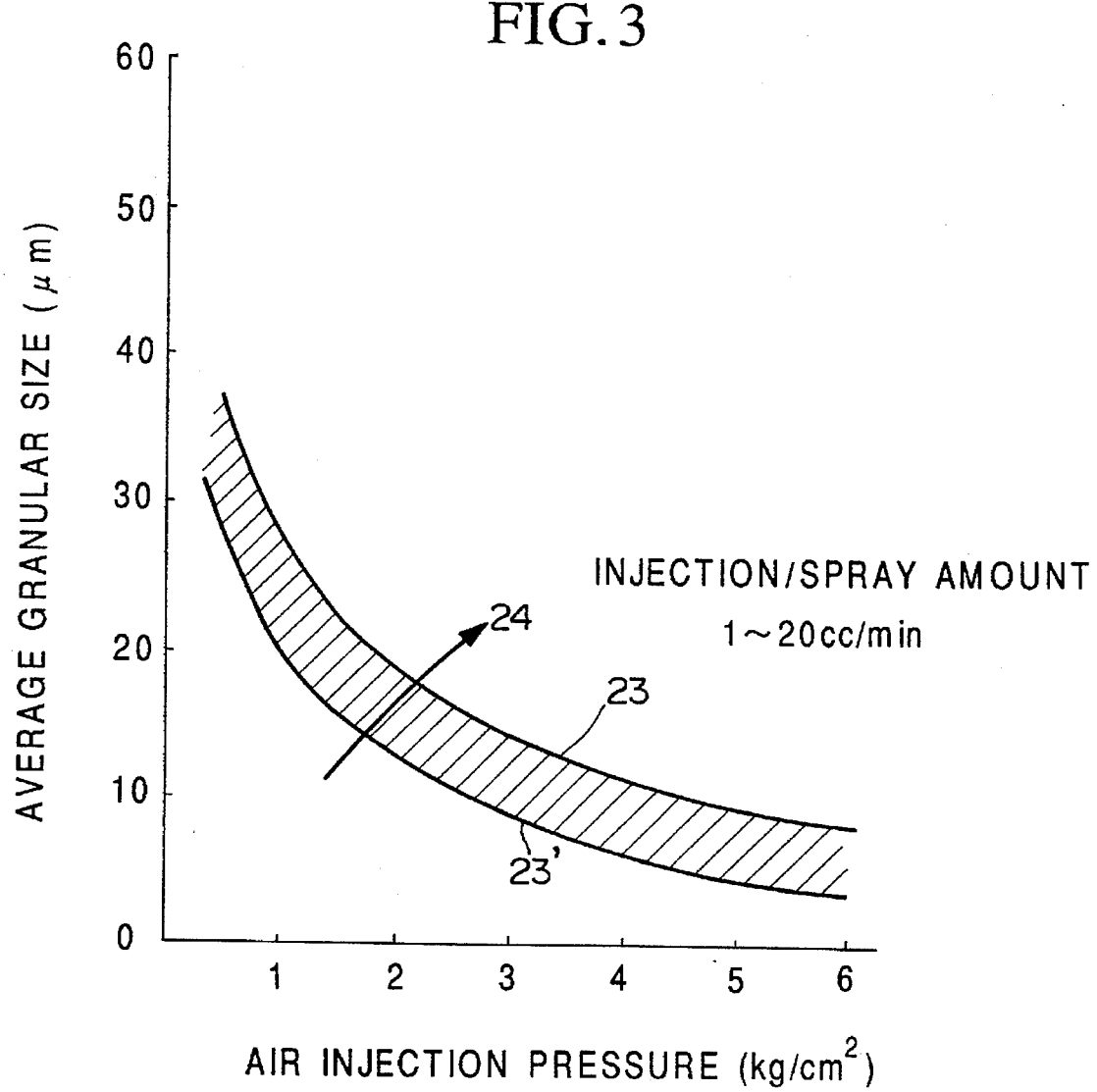

GRANULAR DIAMETER

GRANULAR DIAMETER

FREEZE-DRIED BLOOD CELLS, STEM CELLS AND PLATELETS, AND MANUFACTURING METHOD FOR THE SAME

BACKGROUND OF THE INVENTION

1. Field of the Invention

The present invention relates to freeze-dried blood cells, stem cells, and platelets, and a manufacturing method for the same which does not require a special cooling medium and/or device during cooling such that only a small amount of energy is required wherein mixing/removal of a cryoprotectant such as glycerol or the like is unnecessary.

2. Relevant Art

With regard to maintaining one's own blood for transfusion in times of necessity, and rare blood stored in case of emergency for persons possessing rare blood types, blood for general transfusion, as well as the blood components of the aforementioned all require storage. This storage period usually involves time periods of at least one month.

In the long-term storage of blood and blood components, a freezing process for freezing the aforementioned to −80° C. using an electric freezer, a freezing process using liquid nitrogen (approximately −196° C. storage), and a freezing process using liquid helium (−270° C. storage) represent known methods. All of these blood storage methods require a special cooling medium, container for cooling, and a supply of energy for executing the aforementioned cooling. In addition, before freeze storage, it is necessary to mix some cryoprotectants, compounds that protect living cells against the freezing damage of growing ice crystals or some stresses, such as some glycerol solutions with the blood, and then remove this cryoprotectant at the time of usage after thawing.

In addition, in the long-term storage of blood and blood components, these long-term storage methods of blood and blood components are conducted in the following manner.

An example in which concentrated red blood cells (hematocrit value=55~90%) are frozen will be explained hereinafter (hematocrit value is the proportion of blood cell component to overall blood component: the normal hematocrit value of blood of a healthy person is approximately 45~50%).

1) Using sodium citrate or heparin as an anticoagulant, blood drawn from donors is centrifuged and separated in order to remove plasma and the buffer coat thereby producing concentrated red blood cells possessing a hematocrit value of 55~90%.

2) An equivalent amount of cryoprotectants comprising mainly glycerol is then added to these concentrated red blood cells. This storage solution, for example, may comprise the following:

| | |
|---|---|
| a) glycerol | 60 g |
| b) 70% sodium lactate | 2.57 g |
| c) KCl | 0.02 g |
| d) NaCl | 0.26 g |

The aforementioned composition is dissolved in purified water, and brought to a final volume of 100 ml.

3) The blood after mixing is then placed in a storage vessel and frozen. In the freezing of blood, placed in a container used normally in transfusion (volume 200 ml), the average cooling speed depends on the process; however, a fast process will cool at approximately 100° C./min., while a slow process will cool at several °C./min.

A correlation exists between the cooling speed of the blood, glycerol concentration, and hemolysis (corresponding to the death rate of blood cells) of the blood following thawing. When attempting to restrict the hemolysis to less than a fixed value, in the case of a rapid cooling speed, it is enough to use glycerol of a comparatively low concentration, while in the case of a low cooling speed, it is necessary to use glycerol of a comparatively high concentration. In practice, the following two methods are employed.

a) High-concentration glycerol low freezing speed method b) Low-concentration glycerol high freezing speed method In a), the cryoprotective solution containing glycerol of the composition mentioned in 2) above is added to an equivalent amount of blood, poured into an appropriate container, and placed in an electric freezer at −80° C. At this time, the blood inside the aforementioned container reaches a temperature of −80° C. in a time period ranging from ten minutes to two hours, hence the average cooling speed is 1°~10° C./min. For example, when cooling from room temperature (20° C.) for the one unit of the concentrated red blood cells (≈200 ml), $$\text{average cooling speed} = \{20 - (-80)\}/10 \sim \{20 - (-80)\}/120$$
$$= 10 \sim 0.83$$
$$\approx 1 \sim 10° \text{ C./min.}$$

In the case of b), for example, when a low-concentration glycerol solution of 28% of glycerol, 3% of mannitol, and 0.65% of NaCl is added to an equivalent amount of blood, poured into an appropriate container, and dipped in liquid nitrogen, according to this method, the blood inside the aforementioned container reaches the temperature of the liquid nitrogen (−196° C.) in 1~2 minutes from room temperature. Therefore, the average cooling speed is 2°~4° C./sec for one unit of the blood (≈200 ml).

$$\text{average cooling speed} = \{20 - (-196)\}/60 \sim \{20 - (-196)\}/120$$
$$= 3.6 \sim 1.8$$
$$\approx 2 \sim 4° \text{ C./sec.}$$

4) At the time of usage, after removing the blood from a freezer, rapid thawing is conducted using a water bath of approximately 40° C.

5) After thawing, the glycerol is removed by washing the blood using a physiologically isotonic saline solution such as brine or the like. This process requires several hours to perform.

With regard to the method for granulating the blood, conventionally, a method for performing granulation by means of performing drop-wise addition using a gas in liquid nitrogen is known.

For example, details of the aforementioned method may be found by referencing T. Sato (*A Study of Red Blood Cell Freeze Storage Using Droplet Freezing* [translated]; Journal of the Hokkaido University School of Medicine, vol. 58, No. 2, pages 144~153 (1983)). In this method, a process in which the inflow strength of air is adjusted to produce droplets of various sizes is employed as the method for granulation. In the above case, the size of the droplets for mixing with a gas are rather large, e.g., 0.7~2.8 mm as shown in FIG. 4 of the aforementioned document. The recovery rate [100—(the hemolysis of red blood cells)] is also poor, varying in the 35~70% range. In addition, in the same Figure, when the size is reduced to 0.5 mm, the recovery rate fails below 20% which is impractical for use.

In this method, a double tube formed from a polyethylene inner tube possessing an inner diameter of 0.4 mm surrounded by an outer tube possessing an inner diameter of 3 mm is employed. In this manner, blood is introduced from the inner tube, while gas is introduced from the outer tube. Using Bernoulli's theorem, blood is introduced by generating negative pressure at the output end of the inner tube, and gas is mixed therein. This mixture is then added dropwise to liquid nitrogen which is positioned underneath the aforementioned. The granular size of the blood drops is determined according to the diameter of the inner tube, while the dropwise speed is determined by means of the flow amount of gas flowing into the outer tube.

Consequently, according to this method, as shown in the aforementioned FIG. 4, only large granules of 0.7 mm to 2.8 mm, or granules of an extremely limited range can be formed. As shown in the same Figure, when the diameter of the inner tube is enlarged, the granular size increases, which, in turn, leads to an increase in the hemolysis. In addition, reducing the diameter of the inner tube causes blinding, and dropwise addition of the blood then becomes impossible.

In other words, in the conventional granulation method, due to the use of a simple system of a negative pressure based on Bernoulli's theorem, sufficient control over the granulation cannot be obtained. Hence, disadvantages exist such as a large granular size ranging from 0.7 mm~2.8 mm, such that the formation of granules of 0.5 mm or less is not possible. In the case of a granular size of 0.5 mm, control is difficult leading to an extremely poor recovery rate (i.e., hemolysis is high).

The conventional methods for storing blood described above possess the following drawbacks.

1) The cooling process requires a special cooling medium and container, which in turn require the supply of a large amount of energy. For example, liquid nitrogen and liquid helium are expensive, costing 100 yen per liter and 3,000 yen per liter, respectively, and also require a special container with regard to sealing and cooled insulation.

2) A cryoprotective solution consisting mainly of glycerol is employed, and thus it is necessary to set aside time for removing the glycerol after thawing and before use.

As described in the aforementioned, the conventional blood storage methods pose problems in that these methods require a special cooling medium and container, as well as a large supply of energy. Furthermore, removal of the glycerol is complex and requires time; hence, these methods cannot be applied in case of emergencies or urgent situations.

In addition, the conventional blood freezing method employing a droplet process possesses disadvantages in that, in addition to the large granular size (0.7 mm to 2.8 mm) obtained, a high hemolysis results which cannot be applied to practical use.

SUMMARY OF THE INVENTION

It is an object of the present invention to provide freeze-dried blood cells, stem cells, and platelets, and a manufacturing method for the same, which require only a small amount of energy for storage, and may be stored at normal temperatures or in a standard refrigerator, wherein a process for removing the glycerol is not necessary.

In order to achieve this object, the present invention provides a method for manufacturing freeze-dried blood cells, stem cells and platelets comprising the steps of:

pre-treating a liquid selected from the group consisting of blood including blood cells, bone marrow fluid (hemopoietic stem cells), and platelets in blood plasma, with a solution containing at least one substance selected from the group consisting of saccharide, biopolymer, acid and acid salt;

conducting granulation of said pre-treated liquid into a granules of a first predetermined size;

performing rapid cooling of said granules of the first predetermined size into a frozen product of a second predetermined size; and drying said frozen product by means of sublimation of a water content therein.

According to the present invention, there is also provided a freeze-dried product of one type of liquid selected from the group consisting of blood including blood cells, bone marrow fluid (hemopoietic stem cells), and platelets suspended in plasma; said freeze-dried product being formed from clusters and/or porous substance possessing a size of not greater than 1 mm and comprising granules possessing a size of several μm to several 100 μm.

BRIEF DESCRIPTION OF THE DRAWINGS

FIG. 3 is a graph showing the relationship between average granular size and air injection pressure according to an embodiment of the present invention.

DETAILED DESCRIPTION OF THE INVENTION

In the following, the present invention will be explained in greater detail.

The term "blood" is used in the description of the embodiments and Figures contained hereinafter to mean blood or blood components for the sake of convenience.

In the following, an embodiment of the present invention will be explained, as an example of blood, based on the Figures.

Figure 1:
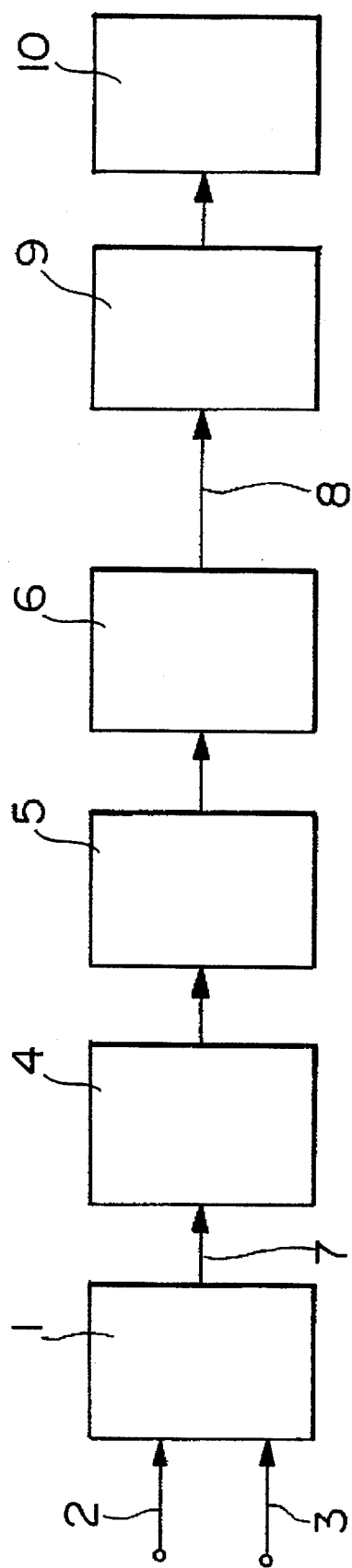
FIG. 1 is a block diagram showing a procedural example of the method of the present invention.

FIG. 1 is a block diagram showing a procedure according to an embodiment of the present invention. In this Figure, a mixing mechanism 1 for mixing blood 2 and pre-treatment additive solution 3; the resultant mixed fluid 7 of this blood and pre-treatment additive solution; granulation mechanism 4 for conducting granulation of mixed fluid 7 of the blood and pre-treatment additive solution; cooling (freezing) mechanism 5 for cooling (freezing) the mixed fluid granulated above; drying mechanism 6; freeze-dried blood 8 obtained for storage; storing mechanism 9 (to be explained hereinafter), and reconstitution mechanism 10 are shown.

As blood 2, concentrated red blood cells, for example, possessing a hematocrit value of 55~90% are employed. At this time, it is possible to pre-treat the aforementioned blood. As an example of pre-treatment additive solution 3, a solution containing at least one type of a saccharide, biopolymer, acid and acid salt can be mentioned. The concentrated red blood cells are then mixed with the aforementioned pre-treatment additive solution, using an appropriate amount of both components. As the process for mixing, any standard method can be employed, such as stirring, agitating, vibration, and the like. In addition, the mixing procedure may comprise pouring the blood into the pre-treatment additive solution, or vice versa. It is preferable that the pre-treatment additive solution be added to the blood while stirring.

The aforementioned saccharide is at least one saccharide selected from among mannose, xylose, glucose, trehalose, sucrose, and maltose.

As the aforementioned biopolymer comprises at least one biopolymer selected from the group consisting of dextran, phosphate, polyvinyl pyrolidone (PVP), and albumin. As the aforementioned phosphate, phosphorylcholine chloride (Sigma reagent no. P0378), 5-phosphorylribose-1-pyrophosphate (Sigma reagent no. P8296), $C_3H_3NO_6P$ (Sigma reagent no. P5506), $C_3H_5NO_6P$ (Sigma reagent no. P0753), $C_3H_8NO_6P$ (Sigma reagent no. P0878), and $C_3H_{10}NO_6P$ (Sigma reagent no. P1003) can be mentioned. Examples of salts of the aforementioned include sodium salts and calcium salts.

As the aforementioned albumin, there can be mentioned at least one type of albumin selected from the group consisting of human albumin, bovine albumin, and egg white albumin.

Examples of the aforementioned human albumin include Sigma reagent no. A-1653, Sigma reagent no. A-1887, Sigma reagent no. A-9511, Sigma reagent no. A-8763, Sigma reagent no. A-3782, Sigma reagent no. A-6784, Sigma reagent no. A-6019, Sigma reagent no. A-6909, dinitrophenol (Sigma reagent no. A-6661), and the like.

In addition, the aforementioned bovine albumin includes Sigma reagent no. A-2153, Sigma reagent no. A-3350, Sigma reagent no. A-4503, Sigma reagent no. A-3425, Sigma reagent no. A-9647, Sigma reagent no. A-8022, Sigma reagent no. A-6003, Sigma reagent no. A-2934, Sigma reagent no. A-9543, Sigma reagent no. A-4628, Sigma reagent no. A-7888, Sigma reagent no. A-4378, Sigma reagent no. A-3424, Sigma reagent no. A-7511, Sigma reagent no. A-7638, Sigma reagent no. A-0281, Sigma reagent no. A-3059, Sigma reagent no. A-3902, Sigma reagent no. A-7906, Sigma reagent no. A-6793, Sigma reagent no. A-6918, Sigma reagent no. A-3912, Sigma reagent no. A-7409, Sigma reagent no. A-7534, Sigma reagent no. A-7284, Sigma reagent no. A-1662, Sigma reagent no. A-3299, Sigma reagent no. A-3174, Sigma reagent no. A-7159, Sigma reagent no. A-7034, Sigma reagent no. A-3294, Sigma reagent no. A-7030, Sigma reagent no. A-9430, Sigma reagent no. A-3803, Sigma reagent no. A-7688, Sigma reagent no. A-3675, Sigma reagent no. A-9306, and the like.

Examples of the aforementioned egg white albumin include Sigma reagent no. A-5253, Sigma reagent no. A-5378, Sigma reagent no. A-5503, Sigma reagent no. A-2512, Sigma reagent no. A-7641, Sigma reagent no. A-3154, and the like.

In addition, examples of the aforementioned acid or acid salt include at least one substance selected from the group consisting of phytinic acid (also known as inositol hexaphosphoric acid: IHP), pyrophosphate, adenosine triphosphosphate (ATP) and 2,3-diphosphoglyceric acid (2,3-DPG).

Examples of the aforementioned pyrophosphate include calcium salts ($Ca_2P_2O_7$), iron salts ($Fe_4(P_2O_7)_3$), potassium salts ($K_4P_2O_7$), sodium salts ($Na_2H_2P_2O_7$ or $Na_4P_2O_7.10H_2O$), tin salts ($Sn_2P_2O_7$), tributyl ammonium salts, and the like.

The pH of pre-treatment additive solution 3 is controlled to a value between 4 and 9, and preferably between 7.0 and 8.0. The reagents used in this process include dipotassium hydrogen-phosphate, and potassium dihydrogen-phosphate. A 1/15 molar concentration solution of each of the aforementioned is formed, and these solutions are mixed to produce a buffer. The pre-treatment additive solution (to be explained hereinafter) is produced using this buffer as a base. The final concentration is adjusted such that a pH of 4 to 9, and preferably a pH of 7.0 and 8.0 results. In the case when a pH is less than 4, there is a tendency for the cell membrane to harden leading to deterioration of the deformation characteristics. In addition, there exists a tendency for the cell membrane to dissolve at a pH of greater than 9.

Figure 2:
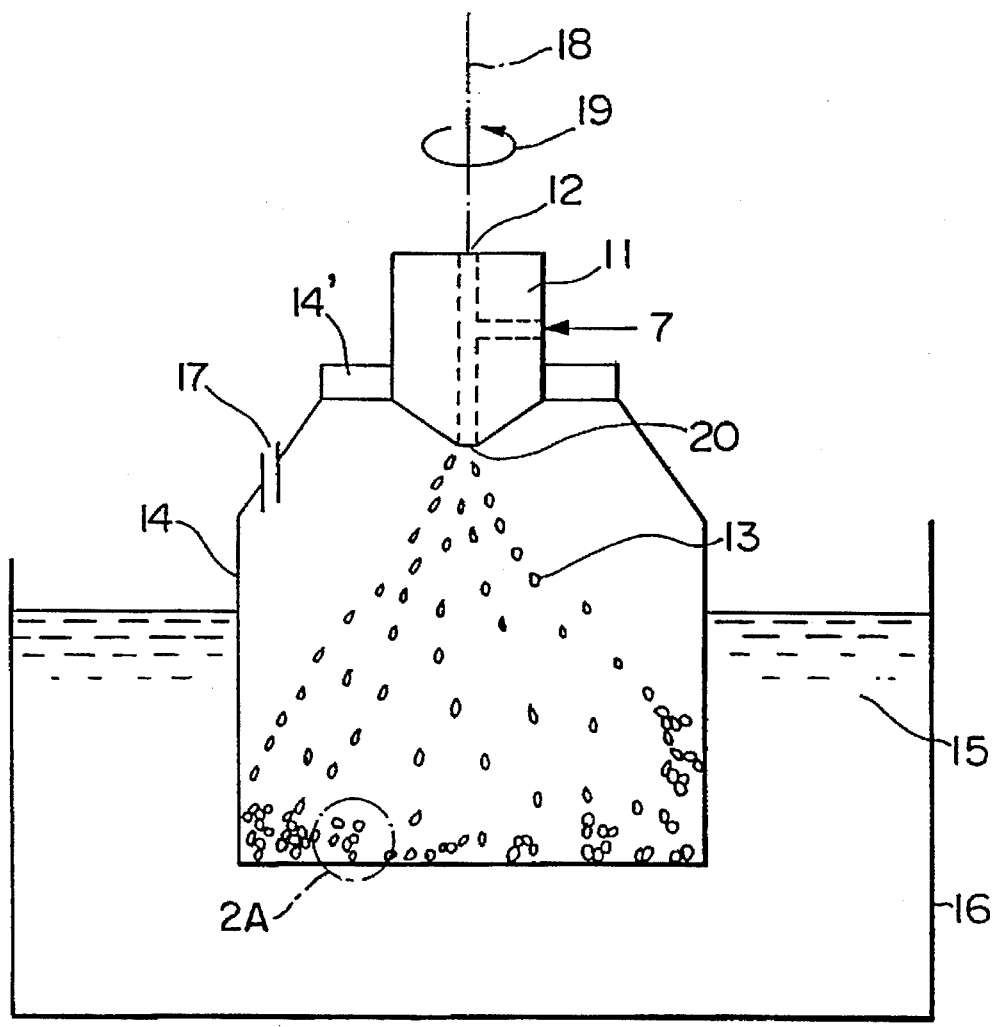
FIG. 2 is a cross sectional diagram showing an example of a device for conducting granulation and rapid freezing according to the present invention, and the granule movement.
Figure 2A:
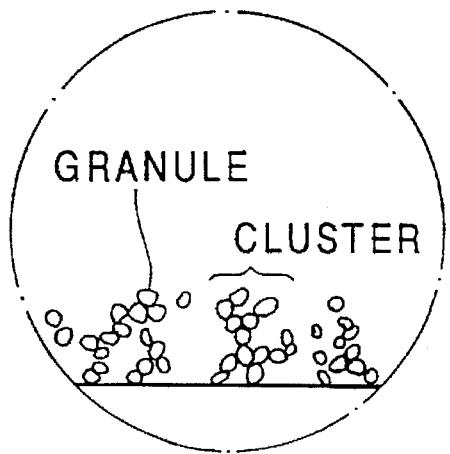
Figure 4:
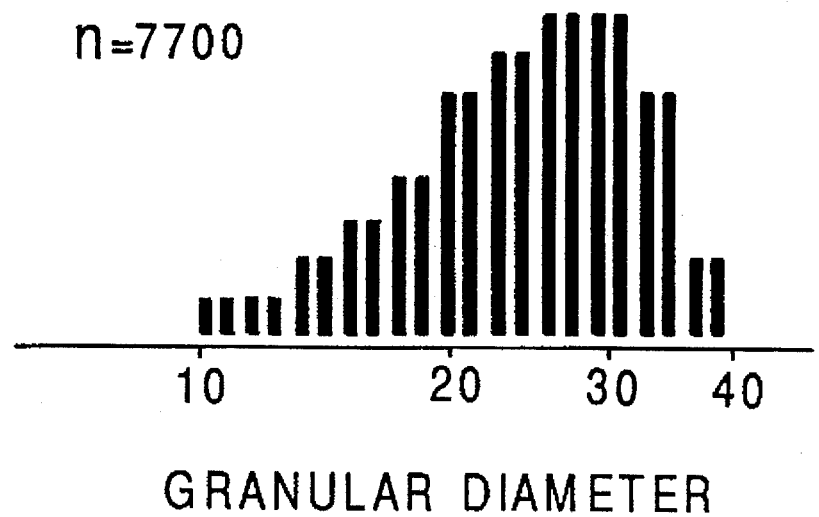
FIG. 4 is a diagram showing the granular size distribution at the outlet of nozzle in the case when conducting granulation of a fluid containing blood at an air pressure of 1 kg/cm$^2$ using the nozzle shown in FIG. 3.
Figure 5:
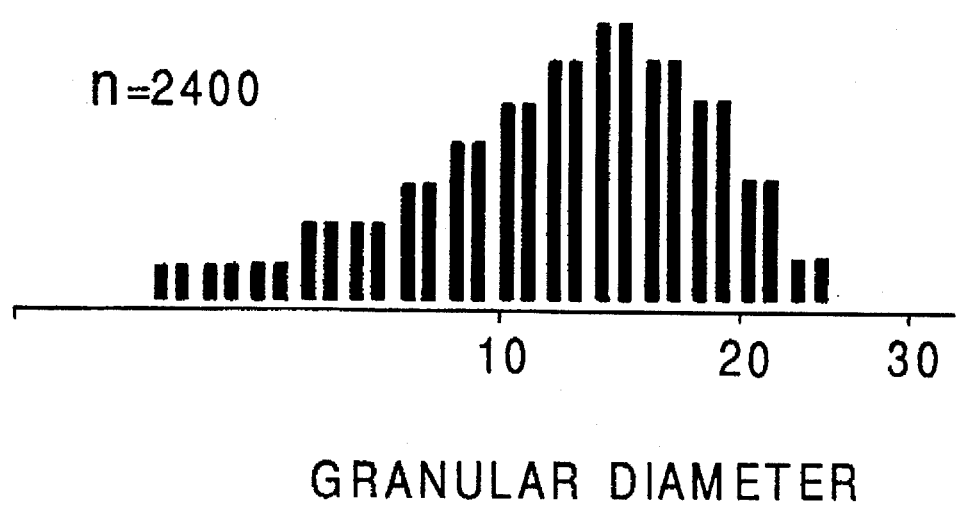
FIG. 5 is a diagram showing the granular size distribution at the outlet of nozzle in the case when granulation is conducted on a fluid containing blood at an air pressure of 4 kg/cm$^2$ using the nozzle shown in FIG. 3.

Granulation mechanism 4, as shown in FIG. 2, may comprise, for example, mixed spraying of a gas such as air, nitrogen gas, or the like, and blood (the aforementioned mixed fluid). It is possible to conduct the granulation by means of a head component driven using ultrasound.

FIG. 2 is a cross sectional diagram showing an apparatus for conducting granulation and rapid freezing according to an embodiment of the present invention, and the movement of the resultant granules.

In FIG. 2, a nozzle 11, gas 12, scattered mixed fluid 13, container 14 for blood recovery, lid 14', cooling medium 15, container 16 for cooling, aperture 17 for gas recovery, rotational axis 18 of container 14, rotational direction 19, and nozzle diameter 20 are provided. As shown in FIG. 2, mixed fluid 7 undergoes scattering-granulation by means of mixing with gas 12 via nozzle 11. The scattered mixed fluid 13 is shown in the same Figure. Container 14 for using blood recovery is cooled by means of a cooling medium 15 such as liquid nitrogen or the like which is placed in container 16 for cooling. Scattered mixed fluid 13 is rapidly cooled via the inner wall of container 14 for use in blood recovery.

According to conventional cooling methods, even with regard to the aforementioned rapid cooling methods, in the case of granulation, in addition to a high heat conductivity (even in the case when the cooling speed per unit volume is the same), since the volume itself is small, the cooling speed per granule becomes extremely large.

For example, when estimating the cooling speed ratio taking into consideration only the effects of volume, the comparison of the average cooling speed with blood (above-described case) of volume 200 ml results in the following calculation:

$$\begin{aligned}\text{average cooling speed ratio} &= v \text{ (cooling speed of a 200 ml packed cells)}/v \\ &\quad \text{(cooling speed of spheres of radius 10 } \mu\text{m)} \\ &= 200/(4\pi (10 \times 10^{-4})^3/3) \\ &= 5 \times 10^{10}\end{aligned}$$

In other words, $5 \times 10^{10}$ times the aforementioned.

In actuality, granules are scattered one after another on top of the frozen granules adhering to the inner wall of the container, thus granules successively accumulate while maintaining their granular shape to form large aggregates, i.e., large branch-shaped clusters as representatively shown in the enlarged view illustrated by means of FIG. 2. In addition, alternatively, it is possible to form a porous product possessing a large number of pores. Consequently, the cooling speed of these granules forming the above-described clusters or porous product, is smaller than the aforementioned ratio of $5 \times 10^{10}$. Due to the absence of an actual mechanism for measuring this quantity, it is difficult to provide exact figures, however, a ratio of at least approximately $10^3$ to $10^6$, in other words, a cooling speed of 1,000° C./sec. to several million °C./sec. is estimated.

Consequently, since the cooling speed is sufficiently greater than the crystal formation speed Of ice from the water contained in the above-mentioned blood, during freezing, large granules of ice are not formed, and the blood (blood cells) are frozen without being damaged. This high-speed cooling contributes to an even greater recovery rate of blood cells when combined with the aforementioned pre-treatment additive solution. By means of providing a mechanism rotating (19) around axis 18 in order to maintain a constant cooling speed, it is possible to maintain equivalent cooling conditions for blood adhering to container 14 for use in blood recovery. In container 14 for blood recovery, an aperture 17 for gas recovery is provided which serves as a mechanism restricting the rise of pressure within the container. Consequently, by means of the aforementioned structure, it is possible to granulate and cool a large amount of blood. In addition, container 14 for blood recovery possesses a sterilized structure.

In order to increase the cooling efficiency, it is possible to rotate container 14, and/or tilt container 14 during rotation. In addition, in a sterile sealed container, it is also possible to conduct instant recovery by spraying into a rotating cooling can using a blade when necessary; conduct recovery by spraying onto a cooling plate possessing a plate shape, and imparting a relative speed when necessary; conduct instant recovery using a blade and imparting a relative speed when necessary using a plurality of nozzles; and/or conduct instant recovery using only a blade.

The aforementioned nozzle 11 preferably possesses the following mechanisms. In other words, in the nozzle for ultra-fine granule generation by means of high-speed vortex gas disclosed in Japanese Patent Application, Second Publication, No. Hei 4-21551 (publication date: Apr. 10, 1992/Japanese Patent No. 1730868), there are provided a liquid injection nozzle; a ring-shaped vortex chamber formed at a position matching the aforementioned liquid injection nozzle; a plurality of turning introduction apertures extending in a vortex manner to the vortex chamber for introducing a high speed air current into the aforementioned vortex chamber; and ring-shaped gas injection nozzle, opening out in front of the liquid injection nozzle and facing the aforementioned liquid injection nozzle side of the vortex chamber, for projecting and forming a thin conical high-speed vortex possessing a focus in front of the liquid injection nozzle. In addition, it is also possible to use nozzles possessing similar functions disclosed in Japanese Patent No. 1689645, Japanese Patent No. 1689660, Japanese Patent No. 1757351, and Japanese Patent No. 1770496. These aforementioned documents disclose various examples of gas and liquid introduction methods.

In the aforementioned structure, whereas the nozzle is not structure of the nozzle is not shown precisely in FIG. 2, the pulverization•granulation of a fluid is conducted by means of forming a gas introduced from a gas introduction port by means of a plurality of turning introduction apertures extending in a vortex manner to the vortex chamber for introducing a high-speed gas flow into the vortex chamber; the resultant gas vortex passes through the vortex chamber and is projected from the thin conical ring-shaped gas injection nozzle possessing a focus in front of the liquid injection nozzle to generate a high-speed vortex. In this manner, the aforementioned fluid pulverization•granulation is conducted. By means of this type of nozzle, it is possible to conduct granulation of a fluid including blood (to be described hereinafter). In addition, the distribution of the aforementioned granular size is narrow, and thus it is possible to, more importantly, conduct granulation to produce granules of approximately the same size.

The aforementioned blood is scattered in liquid drops (i.e., aggregate of a plurality of blood cells possessing a large granular shape) of a granular size which differs depending on the pressure 12 of the gas to mixed in and the nozzle diameter 20. For example, in a case when a nozzle possessing a nozzle diameter of 1.2 mm is used, the relationship between the pressure of the gas and the aforementioned granular size is as shown in FIG. 3. The vertical axis represents average granular size (μm), while the horizontal axis represents the air projection pressure (kg/cm$^2$) 23, 23', wherein curved lines displaying the relationship between both gas pressure and granular size are formed. The hatched portion of FIG. 3 represents 1~20 cc/min. of the blood-mixed fluid. In the example shown in FIG. 3, i.e., in the case when the nozzle diameter was 1.2 mm, granules obtained over the air injection pressure range of 0.5~6 kg/cm$^2$ possessed a size of approximately several microns to 40 μm, and were scattered and adhered to the container. As the nozzle diameter increases, curved line 23 moves in the direction indicated by arrow 24, and hence, it is possible to control the granular size and processing amount of the mixed fluid. In the aforementioned, "granule" refers to the product scattered from the above-described nozzle, and "cluster" signifies an aggregate of a plurality of these granules.

FIGS. 4 and 5 show examples in which liquids containing blood have been granulated at an air pressure of 1kg/cm$^2$, and 4 kg/cm$^2$, respectively, using the nozzle described in FIG. 3, and then measured using a dust measuring instrument employing a laser. As seen from the Figures, the obtained granular size is as small as several 10 μm, resulting in a sharp distribution and superior uniformity of size. Furthermore, in FIGS. 4 and 5, n represents the number of granules to be measured.

As seen from FIG. 3, it is possible to control the granulation by means of the gas pressure and liquid flow amount with respect to a given nozzle diameter. It is also possible to control the granulation mentioned above by means of increasing/decreasing the nozzle diameter. In addition, control of the granular size between several microns and several hundred microns is possible by means of an injection nozzle; however, in the case of red blood cells, with respect to a cell size of preferably 10 μm to 200 μm (diameter of the granules), favorable results can be obtained using an injection nozzle which possesses a diameter corresponding to approximately a few to several tens of cells.

As described above, the granules scattered from the injection nozzle are cooled (frozen) by successively adhering to the container wall. Consequently, in the frozen blood, individual granules accumulate (retaining their original granular shapes) and bond to form branch-shaped clusters. In addition, in the case of concentrated accumulation of these granules, porous products possessing a large number of pores can be formed.

For example, in the case when granules scattered by means of the injection nozzle are formed at a granular size of approximately 30 µm, branch-shaped clusters or porous products are formed containing approximately several 10 to several 100 granules. Observation under an electron scanning microscope reveals branch-shaped clusters and/or porous products ranging in size from 100 to several hundred microns, i.e., overall size of product following freeze-drying of 1 mm or less (to be explained hereinafter).

On the other hand, as shown by means of the Comparative Examples, in the case when granulation according to the present invention is not performed, instead of formation of the products described above, bulk solids are obtained, thus limiting the storage and reconstitution processes. In addition, in the case of independent granules possessing a granular size of approximately 30 µm or less (i.e., in the case when clusters are not formed), due to the formation of a light-weight powder following freeze-drying, these granules are scattered easily, and hence extremely difficult to handle.

Furthermore, as a method which differs from the granulation and freezing methods mentioned above, it is also possible to use a method in which small granules of blood are frozen by means of spraying blood into a gas of a temperature of at least below the freezing point. This method is termed "ice scriber" and includes a method for forming small, frozen granules by means of introducing a liquid into a nitrogen gas at a temperature of liquid nitrogen.

Furthermore, it is ideal to conduct a spraying process in combination with each of the aforementioned methods.

Following completion of an adhering process, lid 14' is immediately removed and container 14 for blood recovery is placed in vacuum mechanism 6. It is possible to use a conventional vacuum dryer (not shown in the Figures) as this aforementioned drying mechanism 6. Since the adhered/frozen blood is at an extremely low temperature, the manufacture of freeze-dried blood 8 is completed by means of conducting dehydration by means of a sublimation process in the aforementioned dryer. At this time, as described above, branch-shaped clusters or porous products are formed possessing a size of several hundred microns.

It is possible to store freeze-dried blood 8 in a standard refrigerator (storage temperature of approximately 5° C.). At the time of use, the freeze-dried blood is reconstituted by means of reconstitution mechanism 10 shown in FIG. 1, and after washing, this reconstituted blood can be used in transfusion and the like.

EXAMPLES

In the following, the present invention will be concretely described by means of the Examples. The present invention is, however, not limited to these examples.

In the following Examples 1 to 7 and Comparative Examples 1 to 3, xylose, glucose, mannose, and disaccharide of 1 to 2 Mol. and PVP possessing a molecular weight of approximately 40,000 were used. In addition, similar results were obtained using pyrophosphate as with each of sodium, calcium, potassium, and iron salts.

Example 1

The present Example relates to the recovery rate of blood cells at the time of reconstitution after storing. A pre-treatment additive solution of a representative composition shown in Table 1 (to be described hereinafter) is prepared and mixed with an equivalent amount of blood (concentrated red blood cells: hematocrit value=55%~90%), following which granulation•freeze-drying is conducted. The air injection pressure and fluid (blood) injection amount were respectively set to 1 Kg/cm$^2$ and 20 cc/min., thus the granular size at the nozzle output end was estimated to be, on average, approximately 30 to 40 µm. In this manner, as the product following freeze-drying, branch-shaped clusters of 300 to 700 µm were obtained. The water content incorporated at the time of drying was 0~30%. The resultant blood was stored in a standard refrigerator (temperature 5° C.) for 1 month, and then reconstituted by adding the pre-treatment additive solution in an amount identical to that at the time of mixing (samples #1 and #2). At this time, due to the excellent concordance with the reconstitution solution, the freeze-dried blood dissolved easily and successful reconstitution was observed. Samples #3 and #4 which were stored for 3 months were also prepared. Each resultant blood was centrifuged for 10 minutes at 2,000 rpm, the supernatant was collected, and the hemoglobin was measured using a blood cell counter (Sysmecs NE-8000). This measured result was then divided by the hemoglobin count of the mixed fluid before granulation•freeze-drying (previously measured value) to produce the hemolysis. The hemolysis at this time was close to the recovery rate following granulation•freeze-drying. The recovery rate equals 100—(hemolysis) (%).

Comparative Examples 1 and 2

In Comparative Examples 1 and 2, each experiment was conducted without performing the granulation by means of the aforementioned process, in which after placing a blood-mixed fluid of the same composition as above into a flask, freeze-dried blood was manufactured according to the same techniques. The resultant product was a dried bulk solid possessing a shape similar to that of the inner shape of the container (granular size does not exist due to the omission of the granulation process). This freeze-dried blood was reconstituted (storage period one month) according to the same techniques as above. This aforementioned product did not dissolve easily when immersed and mixed in the reconstitution solution. Hence, the dissolution (reconstitution) required a large amount of time. In addition, the same experiment (Comparative Example 3) was repeated using a pre-treatment additive solution containing only glucose. These results are shown in the following Table I.

TABLE I

| Sample | Pre-treatment additive solution | | | Recovery rate |
|---|---|---|---|---|
| | Saccharide | Biopolymer | Acid Salt | |
| #1 | Glucose | 12% PVP | 0.5% Pyrophosphate | 60–95% |
| #2 | Xylose | 12% PVP | 0.5% Pyrophosphate | 60–75% |
| #3 | Glucose | 12% PVP | 0.5% Pyrophosphate | 60–95% |
| #4 | Xylose | 12% PVP | 0.5% Pyrophosphate | 60–75% |
| Comp. Ex. 1 | Glucose | 12% PVP | 0.5% Pyrophosphate | 5–15% |
| Comp. Ex. 2 | Xylose | 12% PVP | 0.5% Pyrophosphate | 5–10% |
| Comp. Ex. 3 | Glucose | — | — | <5% |

Example 2

With regard to samples #1 to #4 in Example 1, granulation followed by freezing and drying was performed using an ink-jet head employed in a character printer as the nozzle of Example 1. The nozzle diameter was 100 µm. The aforementioned ink-jet head was driven by means of an ultrasonic component, and the driving frequency was 30~80 kHz. The pretreated blood was then sent into an ink cartridge, and granulation was conducted. The size of the blood varied depending on the driving frequency. The range for the present experiment resulted in a granular size of approximately 5~30 µm.

Subsequently, upon measuring the red blood cell recovery rate following freeze-drying (100—hemolysis)%, an excellent result of 75~95% was obtained. In the same manner as above, branch-shaped clusters, possessing a size of 100 μm or less, were formed in the present experiment. As shown by the aforementioned results, the freeze-dried blood of the present invention possessed a superior storage stability and sufficient recovery rate for practical use. Therefore, this freeze-dried blood can be applied during actual transfusion.

In the following Examples 3~5, the molecular weight for each of PVP, phosphate, and dextran was approximately 40,000. In this manner, similar results were obtained using phosphate as in the case of sodium salts and calcium salts, respectively. In addition, similar results were obtained using pyrophosphate as in the case of sodium salt, potassium salt, calcium salt, and iron salt.

Example 3

The pre-treatment additive solution of the composition shown in Table 2 was prepared, mixed with an equivalent amount of blood, and then granulated •freeze-dried. The granulation•rapid cooling speed was 1,000° C./sec.~several 1,000,000° C./sec., which was approximately thousand to several million times the cooling speed of the conventional technique. The water content incorporated at the time of drying was 0~30%. The resultant branch-shaped clusters of blood were stored for one month in a standard refrigerator (temperature 5° C.), and then reconstituted by means of adding pre-treatment additive solution in an amount identical to that at the time of mixing. The resultant blood was then centrifuged for 10 minutes at 2,000 rpm, the supernatant was collected, and a hemoglobin content was taken using a blood cell counter (Sysmecs NE-8000). This measurement was then divided by the hemoglobin content of the mixed liquid (previously measured) before granulation•freeze-drying to produce the hemolysis. The hemolysis at this time was very close to the recovery rate following granulation•freeze-drying. These results are shown in Table 2 below.

TABLE II

Pretreatment additive solution

| Saccharide | Biopolymer | Acid or Acid Salt | Recovery rate |
|---|---|---|---|
| Xylose | 20% PVP | 2% IHP | 60–70% |
| Mannose | 20% PVP | 2% IHP | 55–65% |
| Glucose | 20% PVP | 0.8% Pyrophosphate | 60–95% |
| Xylose + Mannose | 20% PVP | 2% IHP | 60–65% |
| Disaccharide*[1] | 20% PVP | 2% IHP | 30–55% |

*[1]At least one type of saccharide selected from among trehalose, sucrose and maltose.

Example 4

With the exception of changing the type of biopolymer used in the pre-treatment additive solution employed, the experiment was conducted according to the same method as in Example 3. The results are shown in Table III below.

TABLE III

Pre-treatment additive solution

| Saccharide | Biopolymer | Acid or Acid Salt | Recovery rate |
|---|---|---|---|
| Xylose | Phosphate | 2% IHP | 50–65% |
| Xylose | 12% PVP | 2% IHP | 55–70% |
| Glucose | 20% PVP | 0.8% Pyrophosphate | 40–60% |
| Glucose | 20% Dextran | 2% IHP | 10–35% |

Example 5

With the exception of changing the type of acid or acid salt used in the pre-treatment additive solution employed, the experiment was conducted according to the same method as in Example 3. Furthermore, the concentrations of each component were as follows. The results are shown in Table IV below.

| Saccharide | 1 to 2 Mol. |
|---|---|
| Phosphate | 15% by weight |
| ATP | 1.0% by weight |
| 2,3-DPG | 1.0% by weight |

TABLE IV

Pre-treatment additive solution

| Saccharide | Biopolymer | Acid or Acid Salt | Recovery rate |
|---|---|---|---|
| Xylose | 12% PVP | 2% IHP | 55–70% |
| Xylose | 12% PVP | 0.5% Pyrophosphate | 55–70% |
| Xylose | 12% PVP | 1% Pyrophosphate | 40–70% |
| Glucose | 12% PVP | ATP | 50–85% |
| Xylose | 12% PVP | 2,3-DPG | 60–75% |

The blood following reconstitution in the aforementioned Examples was then washed using a physiological saline solution or the like and applied to actual transfusion to produce excellent results.

In the following Examples 6~8 and Comparative Example 4, the molecular weight of each of PVP, phosphate, and dextran was 40,000. In this manner, similar results were obtained using phosphate as in the case of sodium salts and calcium salts, respectively. In addition, similar results were obtained using pyrophosphate as in the case of sodium salt, potassium salt, calcium salt, and iron salt. In addition, the pH value was mainly 7.4, and the recovery rate of fluids with varying pH from 4 to 9 following freeze-drying, storage and reconstitution resulted in similar values.

Example 6

A pure blood composition (concentrated red blood cells) and the pre-treatment additive solution shown in Table V were respectively prepared, and mixed with an equivalent amount of blood. Granulation•freeze-drying were then conducted on these respective preparations. The granulation•rapid cooling rate was $10^3$° C./sec.~$10^{6°}$ C./sec., which when compared with the cooling speed of the conventional technique, resulted in a speed $10^3$~$10^6$ times as fast as the aforementioned. The water content incorporated at the time of drying was 0~30%. After the resultant dried blood (product resembling branch-shaped clusters) was stored in a standard refrigerator (temperature 5° C.) for one month, the pure blood preparation was reconstituted using an equivalent amount of the pre-treatment additive solution, while the pre-treated preparation was reconstituted using pre-treatment additive solution in an amount identical to that at the time of mixing. The resultant blood preparations were then centrifuged for 10 minutes at 2,000 rpm, and the supernatant of each was collected. The hemoglobin contents were then taken by means of a blood cell counter (Sysmecs: NE-8000). These values were divided respectively by the hemoglobin content of the mixed fluid (mixed fluid of the concentrated red blood cells and pre-treatment additive solution, respectively), previously measured prior to granulation•freeze-drying to obtain a hemolysis for each. Based on the hemolysis at this time, the recovery rates following granulation•freeze-drying were confirmed to be close to (100—hemolysis) %. These results are shown in Table V.

TABLE V

| Pre-treatment additive solution | | | |
|---|---|---|---|
| Saccharide | Biopolymer | Acid or Acid Salt | Recovery rate |
| (Only concentrated red blood cells) | | | 20–30% |
| Glucose | — | — | 40–70% |
| — | 20% PVP | — | 30–60% |
| — | — | 0.5% IHP | 25–30% |
| Glucose | 20% PVP | 0.5% IHP | 95%+ |
| Mannose | 20% PVP | 0.3% IHP | 55–65% |
| Xylose | 20% PVP | 0.5% Pyrophosphate | 60–80% |
| Xylose + Glucose | 20% PVP | 0.5% IHP | 90%+ |
| Disaccharide*[1] | 20% PVP | 0.3% IHP | 30–55% |

*[1] At least one type of saccharide selected from among trehalose, sucrose and maltose.

Example 7

With the exception of changing the type of biopolymer used in the pre-treatment additive solution employed, the experiment was conducted according to the same method as in Example 6. The results are shown in Table VI below.

TABLE VI

| Pre-treatment additive solution | | | |
|---|---|---|---|
| Saccharide | Biopolymer | Acid or Acid Salt | Recovery rate |
| Xylose | Phosphate | 0.5% IHP | 50–65% |
| Xylose | 12% PVP | 0.8% IHP | 70–85% |
| Glucose | 20% PVP | 0.5% Pyrophosphoric acid | 95%+ |
| Glucose | 20% Dextran | 0.5% IHP | 85–95% |

Example 8

With the exception of changing the type of acid or acid salt used in the pre-treatment additive solution employed, the experiment was conducted according to the same method as in Example 6. Furthermore, the concentrations of each component were as follows. The results are shown in Table VII below.

| Saccharide | 1 to 2 Mol. |
|---|---|
| Phosphate | 10% by weight |
| ATP | 1.0% by weight |
| 2,3-DPG | 1.0% by weight |

TABLE VII

| Pre-treatment additive solution | | | |
|---|---|---|---|
| Saccharide | Biopolymer | Acid or Acid Salt | Recovery rate |
| Xylose | 12% PVP | 1% Phosphate | 70%+ |
| Xylose | 12% PVP | 0.5% Pyrophosphoric acid | 70%+ |
| Glucose | 12% PVP | 1% Pyrophosphoric acid | 95%+ |
| Glucose | 12% PVP | ATP | 90%+ |
| Glucose | 12% PVP | 2, 3-DPG | 90%+ |

The blood of the above Examples following reconstitution was washed with a physiologically isotonic saline solution or the like and then used in actual transfusion to produce excellent results.

Comparative Example 4

The concentrated red blood cells of Table V were frozen (freezing time required was several minutes) and dried using the slow, conventional cooling speed without conducting granulation. Following drying, a bulk solid resulted which was different from the branch-shaped cluster and/or porous substance described in the above Examples. Subsequently, after storing the freeze-dried cells under the same conditions as above, the blood was treated using a pre-treatment additive solution. This process resulted in the destruction of all blood cells producing a recovery rate of zero.

In the following Examples 9~11 and Comparative Example 5, the human albumin and bovine albumin employed each possessed a molecular weight of 66,000. Hence, similar results were obtained using the human albumin, and likewise for the bovine albumin. In addition, similar results were observed even in the case when at least two types of albumin selected from among human albumin, bovine albumin and egg white albumin were used in a mixture. The pH mainly resulted in a value of 7.4: similar values were also obtained for the recovery rate following freeze-drying/storage/reconstitution in the case when solutions of pH values between 4 and 9 were used.

Example 9

A pure blood composition (concentrated red blood cells) and the pre-treatment additive solution shown in Table VIII were respectively prepared, and mixed with an equivalent amount of blood. Granulation•freeze-drying were then conducted on these respective preparations. The granulation•rapid cooling rate was $10^{3°}$ C./sec.~$10^{6°}$ C./sec., which when compared with the cooling speed of the conventional technique, resulted in a speed $10^3$~$10^6$ times as fast as the aforementioned. The water content incorporated at the time of drying was 0~30%. It was confirmed that the shape of the resultant dried blood resulted in branch-shaped clusters or porous products possessing a size of several hundred microns. After the resultant dried blood was stored in a standard refrigerator (temperature 5° C.) for one month, the pure blood preparation was reconstituted using an equivalent amount of the pre-treatment additive solution, while the pre-treated preparation was reconstituted using pre-treatment additive solution in an amount identical to that at the time of mixing. The resultant blood preparations were then centrifuged for 10 minutes at 2,000 rpm, and the supernatant of each was collected. The hemoglobin contents were then taken by means of a blood cell counter (Sysmecs: NE-8000). These values were divided respectively by the hemoglobin content of the mixed fluid (mixed fluid of the concentrated red blood cells and pre-treatment additive solution, respectively), previously measured prior to granulation/freeze-drying to obtain a hemolysis for each. Based on the hemolysis at this time, the recovery rates following granulation/freeze-drying were confirmed to be close to (100—hemolysis) %. These results are shown in Table VIII.

TABLE VIII

| Pre-treatment additive solution | | | |
|---|---|---|---|
| Saccharide | Albumin | Acid or Acid Salt | Recovery rate |
| (Only concentrated red blood cells) | | | 20–30% |
| Glucose | — | — | 40–70% |
| Glucose | 5% Albumin | — | 30–90% |
| — | 5% Albumin | 0.5% IHP | 25–30% |
| Glucose | 5% Albumin | 0.5% IHP | 95%+ |
| Mannose | 5% Albumin | 0.3% IHP | 55–65% |
| Xylose | 5% Albumin | 0.5% Pyrophosphate | 60–80% |
| Xylose + Glucose | 5% Albumin | 0.5% IHP | 90%+ |
| Disaccharide*[1] | 5% Albumin | 0.3% IHP | 30–55% |

*[1] At least one type of saccharide selected from among trehalose, sucrose and maltose.

Example 10

With the exception of changing the type of albumin used in the pre-treatment additive solution employed; the experiment was conducted according to the same method as in Example 9. The results are shown in Table IX below.

TABLE IX

| Pre-treatment additive solution | | | |
|---|---|---|---|
| Saccharide | Albumin | Acid or Acid Salt | Recovery rate |
| Xylose | 5% Human Albumin | 0.5% IHP | 50–65% |
| Xylose | 5% Bovine Albumin | 0.8% IHP | 70–85% |
| Glucose | 5% Egg white Albumin | 0.5% Pyrophosphoric acid | 95%+ |
| Glucose | 3% Human Albumin + 3% Bovine Albumin | 0.5% IHP | 85–95% |
| Glucose | 2% Human Albumin + 3% Bovine Albumin + 2% Egg white Albumin | 0.5% IHP | 85–95% |

Example 11

With the exception of changing the type of acid or acid salt used in the pre-treatment additive solution employed, the experiment was conducted according to the same method as in Example 9. Furthermore, the concentrations of each component were as follows. The results are shown in Table X below.

| Saccharide | 1 to 2 Mol. |
|---|---|
| Bovine albumin | 5.0% by weight |

TABLE X

| Pre-treatment additive soution | | | |
|---|---|---|---|
| Saccharide | Albumin | Acid or Acid Salt | Recovery rate |
| Xylose | 5% Bovine Albumin | 1% Phosphate | 70%+ |
| Xylose | 5% Bovine Albumin | 0.5% Pyrophosphoric acid | 70%+ |
| Glucose | 5% Bovine Albumin | 1% Pyrophosphoric acid | 95%+ |
| Glucose | 5% Bovine Albumin | ATP | 90%+ |
| Glucose | 5% Bovine Albumin | 2,3-DPG | 90%+ |

The blood of the above Examples following reconstitution was washed with a physiologically isotonic saline solution or the like and then used in actual transfusion to produce excellent results.

Comparative Example 5

The concentrated red blood cells of Table VIII were frozen (freezing time required was several minutes) and dried using the slow, conventional cooling speed without conducting granulation. The dried blood resulted in a bulk solid substance. Subsequently, after storing the freeze-dried cells under the same conditions as above, the blood was treated using a pre-treatment additive solution. This process resulted in the destruction of all blood cells producing a recovery rate of zero.

Example 12

With the exception of substituting bone marrow fluid extracted from human subjects by means of the following procedure in place of the pure blood composition (concentrated red blood cells) of Example 9, the pre-treatment additive solution shown in Table XI was prepared, mixed with an equivalent amount of bone marrow fluid, and then granulated•freeze-dried according to the same method as in Example 9. The product resulted in branch-shaped clusters possessing a size of several hundred microns. Furthermore, as the albumin contained in the pre-treatment additive solution of Table XI, compositions of at least two types of the above-described bovine albumin and/or human albumin (same or different types of albumin) were respectively employed to produce similar results.

The bone marrow fluid mentioned above includes both an extract taken directly from the bone marrow, and stem cells (peripheral hemopoietic stem cells) which have been mobilized in the peripheral blood from bone marrow by means of a chemical treatment or the like. In the following, an example of the latter will be explained. The present invention is, however, not limited to this example. In addition, details of the aforementioned can be found by referencing C. Shimazaki and M. Nakagawa ("Method for Extracting Autoperipheral Hemopoietic Stem Cells, and Transplant Effects for the Same"; *Transfusion Medicine* [translated] vol. 75, pp.1049: July Edition, 1993).

After conducting extraction using a CS3000-model apparatus (manufactured by Fenwal Co.), 6% HES (hydrooxthyl starch) was added to the blood extract in the transfusion packet. The red blood cells were removed after allowing to sit for one hour. Subsequently, after centrifuging for approximately 10 minutes at 1800 rpm, the PRP (platelet rich plasma) was removed to yield the desired stem cells (peripheral hemopoietic stem cells).

Following freeze-drying and storage for one month in a standard refrigerator (temperature: approximately 5° C.), the stem cells were reconstituted using a liquid of the same composition as the aforementioned pre-treatment additive solution. The resultant stem cells were then observed under a microscope, and a count of the number of normal cells was performed to calculate recovery rate with respect to the initial values (number of normal cells before freeze-drying and after addition of the pre-treatment additive solution).

TABLE XI

| Pre-treatment additive solution | | | |
|---|---|---|---|
| Saccharide | Biopolymer | Acid or Acid Salt | Recovery rate |
| Glucose | 5% Albumin | — | 30–90% |
| Glucose | 5% Albumin | — | 20–95% |
| Glucose | 5% Albumin | 0.5% IHP | 40–90% |
| Mannose | 5% Albumin | 0.5% IHP | 30–70% |
| Xylose | 5% Albumin | 0.5% IHP | 30–70% |
| Glucose + Xylose | 5% Albumin | 0.5% IHP | 30–70% |
| Disaccharide*[1] | 5% Albumin | 0.5% IHP | 20–50% |
| Glucose | 10% PVP*[2] | 0.5% IHP | 40–80% |

*[1] At least one type of saccharide selected from among trehalose, sucrose and maltose.
*[2] Polyvinylpyrolidone (Molecular Weight approx. 40,000)
*[3] Saccharide 1 to 2 Mol.

Comparative Example 6

A conventional freeze-preservation solution, e.g., solution of 5% DMSO (dimethyl sulfoxide), 6% HES (hydrooxthyl starch) and 4% albumin was added to the stem cells extracted (peripheral hemopoietic stem cells) in Example 12 without addition of the pre-treatment additive solution of the present invention, and freeze-drying was performed. The product of this drying resulted in a bulk solid substance. After storing according to the same method as described above, the number of normal cells following reconstitution was examined to reveal a recovery rate of zero.

Example 13

With the exception of substituting a platelet fluid, separated by means of standard procedures following blood extraction and suspended in the same plasma (autoplasma), in place of the pure blood composition (concentrated red blood cells) of Example 9, the pre-treatment additive solution shown in Table XII was prepared, mixed with an equivalent amount of the platelets suspended in plasma, and then granulated•freeze-dried according to the same method as in Example 9. The product resulted in branch-shaped clusters possessing a size of several hundred microns. Furthermore, as the albumin contained in the pre-treatment additive solution, compositions of at least two types (same or different types of albumin) of the aforementioned bovine albumin and/or human albumin were respectively employed to produce similar results.

Following freeze-drying and storage for one month in a standard refrigerator (temperature: approximately 5° C.), the platelets were reconstituted using a liquid of the same composition as the aforementioned pre-treatment additive solution. The resultant platelets were counted using a blood cell counter to calculate a recovery rate with respect to the initial values (number of platelets before freeze-drying and after addition of the pre-treatment additive solution). In addition, upon measuring with a platelet cohesion measuring instrument (produced by CHRONO-LOG Corporation), the resultant values were found to lie close to the normal values.

TABLE XII

| Pre-treatment additive solution | | | |
|---|---|---|---|
| Saccharide | Biopolymer | Acid or Acid Salt | Recovery rate |
| Glucose | — | — | 20–60% |
| — | 5% Albumin | — | 10–50% |
| Glucose | 5% Albumin | 0.5% IHP | 50–90% |
| Mannose | 5% Albumin | 0.5% IHP | 30–70% |
| Xylose | 5% Albumin | 0.5% IHP | 30–70% |
| Glucose + Xylose | 5% Albumin | 0.5% IHP | 30–70% |
| Disaccharide*[1] | 5% Albumin | 0.5% IHP | 20–40% |
| Glucose | 10% PVP*[2] | 0.5% IHP | 40–80% |

*[1] At least one type of saccharide selected from among trehalose, sucrose and maltose.
*[2] Polyvinylpyrolidone (Molecular Weight approx. 40,000)
*[3] Saccharide 1 to 2 Mol.

Results of the Invention

According to the present invention, freeze-dried blood cells, stem cells and platelets can be stored at normal temperatures. In addition, the aforementioned freeze-dried blood cells, stem cells and platelets are able to withstand even longer periods of storage when stably placed and stored in a standard refrigerator. In other words, the present invention does not exhibit the disadvantages of conventional blood storage methods, i.e., need to provide a special cooling medium and container at the time of storage, and demand for a large supply of energy to maintain the storage temperature. Furthermore, a mechanism for removing the glycerol of the conventional method is likewise unnecessary, hence very few constraints exist at the time of use. Consequently, due to the simplicity herein, the present invention is ideal for use during emergency transfusions and the like.

What is claimed is:

1. A method for manufacturing freeze-dried blood cells, stem cells, and platelets, the method comprising the steps of:
   pre-treating a liquid selected from the group consisting of blood including blood cells, bone marrow fluid (hemopoietic stem cells), and platelets in blood plasma, with a solution containing saccharide, biopolymer, and acid and/or acid salt;
   conducting granulation of said pre-treated liquid to yield granules of a first predetermined size, wherein the granulation is conducted by means of mixed spraying with a gas;
   performing rapid cooling of said granules of the first predetermined size into a frozen product of a second predetermined size; and
   drying said frozen product by sublimation of a water content therein.

2. Method according to claim 1, wherein said first predetermined size is several microns to several hundred microns.

3. Method according to claim 2, wherein said first predetermined size is 10 μm to 200 μm.

4. Method according to claim 1, wherein said second predetermined size is 1 mm or less.

5. Method according to claim 4, wherein said second predetermined size is 100 μm to several hundred microns.

6. Method according to claim 1, wherein said rapid cooling is performed by means of spraying said blood into a gas at a temperature below the freezing point.

7. Method according to claim 1, wherein said saccharide is at least one saccharide selected from the group consisting of mannose, xylose, glucose, trehalose, sucrose and maltose.

8. Method according to claim 1, wherein said biopolymer is at least one biopolymer selected from the group consisting of dextran, phosphate, polyvinylpyrrolidone and albumin.

9. Method according to claim 8, wherein said albumin is at least one type of albumin selected from the group consisting of human albumin, bovine albumin and egg white albumin.

10. Method according to claim 1, wherein said acid or acid salt is at least one substance selected from the group consisting of phytinic acid, pyrophosphate, adenosine triphosphate and 2,3-diphosphoglyceric acid.

11. Method according to claim 1, wherein said solution for use in pre-treating has a pH between 4 and 9.

12. Method according claim 11, wherein said solution for use in pre-treating has a pH between 7 and 8.

13. Method according to claim 1, wherein said rapid cooling is performed at a rate of $10^{3\circ}$ C./second to $10^{6\circ}$ C./second.

14. Freeze-dried product of a solution containing saccharide, biopolymer, an acid and/or acid salt and a liquid selected from the group consisting of blood including blood cells, bone marrow fluid (hemopoietic stem cells), and platelets suspended in blood plasma; said freeze-dried product being formed from porous clusters possessing a size of 100 microns to several hundred microns and comprising from about 10 to approximately several hundred granules possessing a size of 10 microns to 200 hundred microns.

15. A method for manufacturing freeze-dried blood cells, stem cells, and platelets, the method comprising the steps of:

pre-treating a material selected from the group consisting of blood including cells, bone marrow fluid (hemopoietic stem cells), and platelets in blood plasma, with a solution containing saccharide, biopolymer, and acid and/or acid salt to yield a pre-treated liquid;

conducting granulation of said pre-treated liquid to yield granules of a first predetermined size, wherein the granulation is conducted by means of mixed spraying with a gas;

performing rapid cooling of said granules of a first predetermined size to produce clusters of a second predetermined size to yield a frozen product; and drying said frozen product by sublimation of a water contained therein.

16. A method for manufacturing freeze-dried blood cells, stem cells, and platelets, the method comprising the steps of:

preparing a container having a wall;

preparing a pre-treatment solution containing saccharide, biopolymer, and acid and/or acid salt;

pre-treating a material selected from the group consisting of blood including cells, bone marrow fluid (hemopoietic stem cells), and platelets in blood plasma, with the pre-treatment solution to yield a pre-treated liquid;

conducting granulation of said pre-treated liquid in the container to yield granules of a first predetermined size, wherein the granulation is conducted by means of mixed spraying with a gas;

performing rapid cooling of said granules of a first predetermined size in the container to produce clusters of a second predetermined size on the wall of the container to yield a frozen product; and drying said frozen product in the container by sublimation of a water contained in said frozen product.

* * * * *

UNITED STATES PATENT AND TRADEMARK OFFICE
CERTIFICATE OF CORRECTION

PATENT NO. : 5,656,498
DATED : August 12, 1997
INVENTOR(S) : Tetsuo IIJIMA et al.

It is certified that error appears in the above-indentified patent and that said Letters Patent is hereby corrected as shown below:

Title Page, Item [75], in the Inventors, line 3, after "Tokyo", delete "," and insert --; Tadamichi Kawada, Urawa,--.

Title Page, Item [73], in the Assignee, line 2, after "Corporation,", insert --Tokyo,--.

Title Page. Item [57], in the Abstract, line 9, before "granules", delete "a".

Claim 12, column 19, line 14, after "according", insert --to--.

Signed and Sealed this

Fourteenth Day of July, 1998

Attest:

BRUCE LEHMAN

*Attesting Officer*   *Commissioner of Patents and Trademarks*